United States Patent [19]
Painchaud et al.

[11] Patent Number: 6,148,226
[45] Date of Patent: Nov. 14, 2000

[54] OPTICAL IMAGING THROUGH SCATTERING MEDIA: FIT TO AN INHOMOGENEOUS DIFFUSION MODEL FOR DIFFERENTIATION

[75] Inventors: Yves Painchaud, Sainte-Marie; Michel Morin, Cap-Rouge; André Parent, Quebec, all of Canada

[73] Assignee: Aerospace Research Technologies Inc., Canada

[21] Appl. No.: 09/023,414

[22] Filed: Feb. 13, 1998

[51] Int. Cl.⁷ ..................................................... A61B 5/00
[52] U.S. Cl. ........................... 600/476; 356/446; 600/473
[58] Field of Search .................................. 600/473, 475, 600/476; 356/446

[56] References Cited

U.S. PATENT DOCUMENTS

| | | | |
|---|---|---|---|
| 5,371,368 | 12/1994 | Alfano et al. | |
| 5,386,827 | 2/1995 | Chance et al. | |
| 5,413,098 | 5/1995 | Benaron | |
| 5,424,843 | 6/1995 | Tromberg et al. | 356/442 |
| 5,427,094 | 6/1995 | Thurston et al. | |
| 5,427,095 | 6/1995 | Thurston et al. | |
| 5,441,054 | 8/1995 | Tsychiya | |
| 5,529,065 | 6/1996 | Tsuchiya | 128/633 |
| 5,555,885 | 9/1996 | Chance | |
| 5,582,169 | 12/1996 | Oda et al. | |
| 5,625,458 | 4/1997 | Alfano et al. | |
| 5,630,423 | 5/1997 | Wang et al. | 128/664 |
| 5,694,938 | 12/1997 | Feng et al. | 128/644 |

OTHER PUBLICATIONS

Michael Patterson, B. Chance, and B.C. Wilson, Time Resolved Reflectance and Transmittance for the Non–Invansive Measurement of Tissue Optical Properties, Jun. 1989.

Primary Examiner—J. Jastrzab
Assistant Examiner—Eleni Mantis Mercader
Attorney, Agent, or Firm—Hoffman, Wasson & Gitler, PC

[57] ABSTRACT

A method of optical imaging through a scattering medium is provided in which a fit is made to an inhomogeneous diffusion model. The method facilitates good differentiation between scattering and absorption. The variation of the diffusion curve associated with the presence of an inclusion is considered rather than the diffusion curve itself. An empirical model is provided which describes the variation of the diffusion curve. A linear curve fitting process is performed to provide two parameters, one parameter associated with the scattering property of the inclusion and the other parameter associated with the absorption property of the inclusion.

14 Claims, 7 Drawing Sheets

OPTICAL IMAGING THROUGH SCATTERING MEDIA: FIT TO AN INHOMOGENEOUS DIFFUSION MODEL FOR DIFFERENTIATION

BACKGROUND OF THE INVENTION

1. Field of the Invention

The present invention relates to an optical method for imaging through a scattering medium in which a fit is made to an inhomogeneous diffusion model. The method provides a simple means to separate the absorption and scattering contributions of inhomogeneities.

2. Background of the Invention

The ability to optically imaging through a scattering medium is of great interest. Potential applications are the non-destructive localization of inclusions or defects in scattering materials such as composites or polymers and the detection of parasites in fish or meat produce. A main target application is breast cancer detection, which is currently carried out mostly with X-rays. X-rays provide good resolution images but with poor contrast between healthy and cancerous tissues. They are also considered as potentially hazardous to humans. This explains that optical imaging through scattering media is an area of research that has created enormous interest.

Obtaining optical images of the interior of a scattering medium such as a breast is complicated by the extensive scattering of light in such a medium, which results in blurring of the image. As a result of such scattering, the trajectory of a photon (i.e. a light particle) can be predicted only on a statistical basis, each photon propagating along a random-like path as shown in FIG. 1. In addition to being randomly redirected by scattering events, each photon also has a probability of being absorbed by the medium.

In a slab of material that is highly scattering and weakly absorbing, such as the human breast, most photons are reflected towards the entrance surface after traveling only a few millimeters into the medium. Other photons are absorbed by the medium or are transmitted to the output surface where they can be detected. For a breast of typical thickness and optical parameters, 0.01 to 1% of the injected photons at a wavelength around 800 nm are transmitted to the output surface.

The transmitted photons can be separated into three categories: ballistic photons that reach the output surface without be scattered, snake photons that are scattered slightly and maintain a fairly rectilinear trajectory, and diffuse photons that are widely scattered and cover a considerable volume element before emerging. FIG. 1 illustrates each of these categories. Ballistic photons do not experience any scattering event and therefore have the potential to produce a very clear image of the breast interior. Unfortunately, for typical breast thickness and optical parameters, no ballistic photons are transmitted. Snake photons have a nearly rectilinear trajectory, and are sufficient in number to produce a relatively clear image. Diffuse photons provide image information of poor quality due to their degree of scattering. Therefore, researchers have focused their efforts on detecting the snake photons and excluding the diffuse photons. Typically this has been done by utilizing time gating techniques.

Time gating is implemented by sending ultra-short laser pulses inside of a scattering medium. When an ultra-short laser pulse is injected at the surface of a scattering medium its component photons propagate along different trajectories. The different times of propagation lead to the emergence from the scattering medium of a temporally broadened pulse which is called the diffusion pulse or the diffusion curve as illustrated in FIG. 1. For a breast of typical thickness and optical parameters, the duration of the diffusion pulse can be as large as several nanoseconds, which is more than 1000 times the width of the entrance pulse, typically less than 1 picosecond. The initial portion of the diffusion curve corresponds to the snake photons with a shorter path, whereas the remainder corresponds to the diffuse photons. By their shorter arrival time at the detector, the snake photons can be isolated and used to construct the image. This technique, known as time gating, created a resurgence of interest in optical mammography in the early 1990s.

Using only snake photons allows the user to generate images with better spatial resolution. However, the relative noise level increases significantly because much fewer photons are detected in this way. This method also does not allow for the determination of the scattering and absorption properties of an inclusion detected within a scattering medium. In order to overcome these limitations, researchers have looked for ways to use the information carried by all photons, i.e., by the whole of the diffusion curve, to obtain images through scattering media, as follows.

The shape and amplitude of the diffusion curve depend on the scattering and absorption properties of the scattering medium. A theoretical model, the diffusion model, can be used to describe the diffusion curve for homogeneous and optically thick slabs having uniform structure throughout. This model is appropriate in the specific case of light transmitted through a human breast. It involves a limited number of parameters that characterize the scattering and absorption properties of the scattering medium. The optical properties of scattering media such as human tissues are usually characterized by three parameters. The absorption coefficient $\mu_a$ is the probability of a photon being absorbed per infinitesimal pathlength. The scattering coefficient $\mu_s$ is the probability of the photon being scattered per infinitesimal pathlength. Finally, the third parameter is the anisotropy factor g which describes the average change in propagation direction associated with the scattering process. In addition to these three parameters, it is useful to define the reduced scattering coefficient as $$\mu_s' = \mu_s(1-g)$$

representing the average distance over which a photon sustains a sufficient number of scattering events to randomize its direction of propagation. The reduced scattering coefficient is the isotropic equivalent of the scattering coefficient and is applicable to the case of thick scattering media. The quantities $\mu_a$ and $\mu_s'$ are the two main optical parameters that describe the light propagation in thick scattering media. Those two parameters appear in the diffusion model suitable for a homogeneous scattering slab.

Researchers have tried to extract imaging information from the whole of the diffusion curve through curve fitting. Curve fitting is a general numerical technique which includes adjusting a mathematical expression on experimental data. The idea of using curve fitting in optical mammography is not new. The diffusion model has been used as the analytical expression (valid only in homogeneous cases), and curve fitting was employed to smooth the experimental data to reduce the level of noise in the time gating approach.

Since the output of the curve fitting is the parameters of the analytical model, and since some of the parameters are the two optical coefficients $\mu_a$ and $\mu_s'$, the process allows for the separation of information about the scattering and absorption in the probed region. Curve fitting can therefore be performed to obtain those optical parameters and to plot their spatial distributions. As a result, more information is obtained since two output images are created instead of only one. Because the analytical expression used in the curve fitting process is the diffusion model, which is valid only in the homogeneous case, problems develop. In particular, non-uniformity in an inhomogeneous medium results in non-uniformity in the spatial distribution of the optical parameters $\mu_a$ and $\mu_s'$. Since non-uniformity is incorrectly described by the model, incorrect $\mu_a$ and $\mu_s'$ distribution are obtained. As a result, an actual spatial variation of the scattering coefficient may result in a variation of $\mu_a$ as outputted by data processing and vice-versa. The foregoing method does not discriminate correctly between scattering and absorbing effects.

There is a need for a method which provides a simple mathematical expression which describes the effect of inclusions on the diffusion curves which will be applicable to generate images of thick inhomogeneous scattering media.

SUMMARY OF THE INVENTION

The foregoing and other deficiencies of the prior art are addressed by the present invention which is directed to an optical method for imaging through a scattering medium in which a fit is made to an inhomogeneous diffusion model. The method facilitates good differentiation between scattering and absorption. The variation of the diffusion curve associated with the presence of an inclusion is considered rather than the diffusion curve itself. An empirical model is provided which describes the variation of the diffusion curve. A linear curve fitting process is performed to provide two parameters, one parameter associated with the scattering property of the inclusion and the other parameter associated with the absorption property of the inclusion.

It is an object of the present invention to provide a method for optical imaging through scattering medium in which fit is made to an inhomogeneous diffusion model.

Another object of the present invention is to provide a method which facilitates good differentiation between scattering and absorption.

Yet another object of the present invention is to provide a method in which the variation of the diffusion curve associated with the presence of an inclusion is considered rather than the diffusion curve itself.

Still another object of the present invention is to provide an empirical model which describes the variation of the diffusion curve.

Another object of the present invention is to provide a linear curve fitting process which produces two parameters, one associated with the scattering property of the inclusion and the other associated with the absorption property of the inclusion.

Still another object of the present invention is to provide significant advantages over previous curve fitting techniques in that the mathematical expression is extremely simple.

BRIEF DESCRIPTION OF THE DRAWINGS

These and other objects and attributes of the present invention will be described with respect to the following drawings in which.

DETAILED DESCRIPTION OF THE INVENTION

As discussed previously, because the diffusion model is valid only in the case of a homogeneous slab of scattering material, the spatial distributions of the scattering and absorption coefficients do not reflect reality. A technique for representing the spatial distributions of the actual coefficients would be a significant asset. To achieve the foregoing, the diffusion model must be enhanced to adequately take into account the inhomogeneous nature of the turbid medium.

The method of the present invention provides a simple mathematical expression describing the relative change in the diffusion curve measured in specific inhomogeneous cases. The simple mathematical expression is an empirical model based on diffusion curve measurements in different situations. A curve fitting process using the inhomogeneous model allows for proper separation of the absorption and scattering contributions on an arbitrary inclusion. More particularly, the empirical model describes the change in the diffusion curve resulting from the addition of an inclusion in a homogeneous slab of scattering medium. Considering only the variations associated with the presence of the inclusion provides a simpler model. The present invention is referred to as a Fit to an Inhomogeneous Diffusion Model (FIDM).

The empirical inhomogeneous diffusion model has been based on limited geometries and measurement schemes. Inclusions of different sizes and optical parameters have been introduced at the center of a homogeneous slab of scattering medium. Diffusion curve measurements have been performed only when the inclusion is on-axis, i.e. when it is along the source-detector line.

Figure 1:
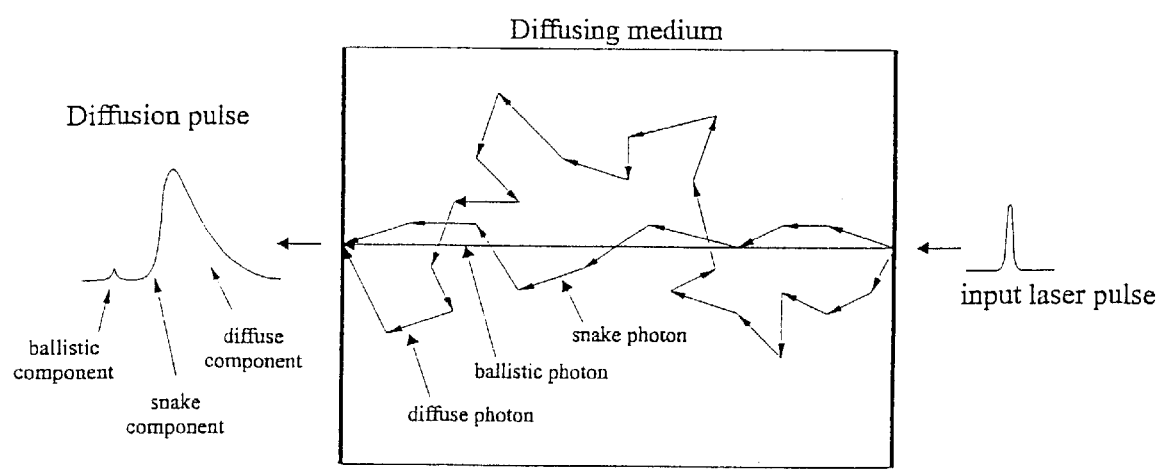
FIG. 1 is a drawing of typical trajectories for the three categories of photons transmitted through a scattering medium as known in the prior art.
Figure 2A:
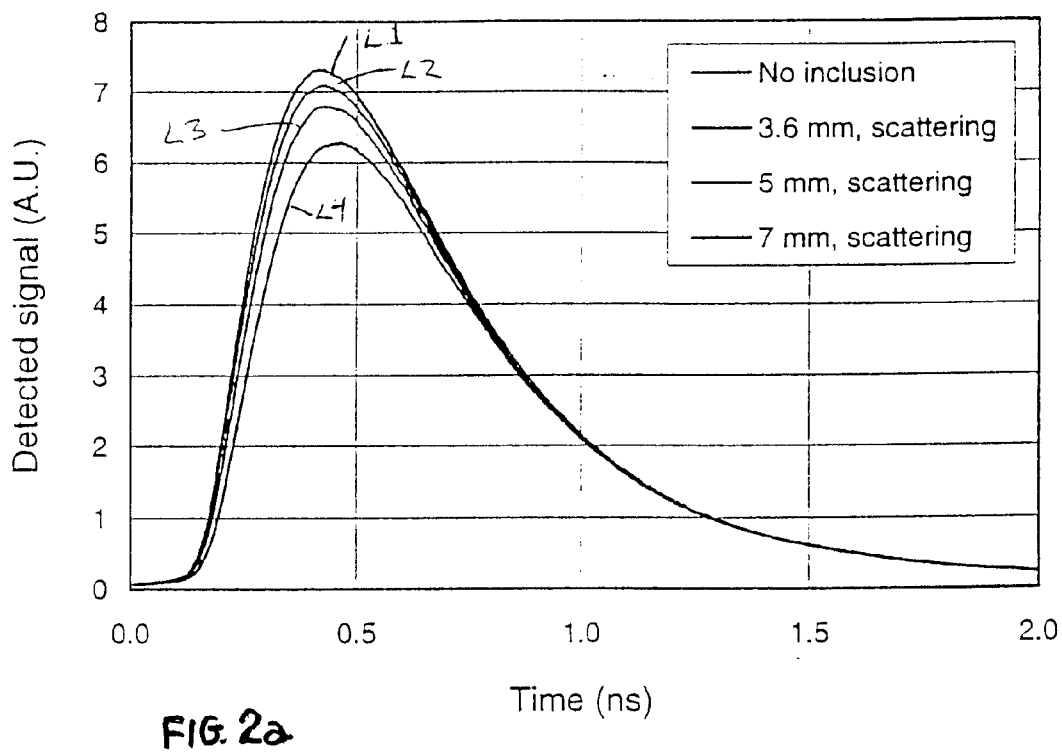
FIGS. 2a and 2b are graphs showing diffusion curves measured through a scattering cell containing scattering and absorbing inclusions.
Figure 2B:
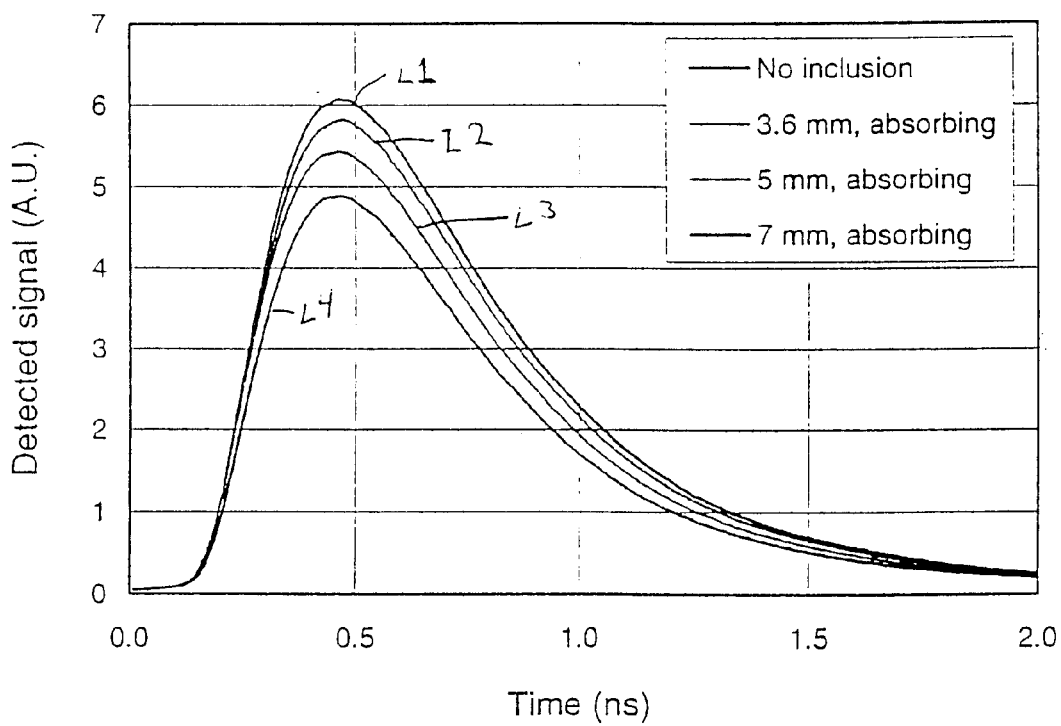

Typical diffusion curves measured through a scattering cell containing scattering and absorbing inclusions are shown in FIGS. 2a and 2b. As shown in these graphs, when the inclusion is scattering, the beginning of the diffusion curve is significantly changed and the tail remains unchanged. An absorbing inclusion has the opposite effect, i.e., the tail of the diffusion curve is strongly attenuated while the beginning is less changed. The diffusion curves were obtained through a 20 mm thick scattering solution ($\mu_s'$=0.97 mm$^{-1}$, $\mu_a$=0.002 mm$^{-1}$) containing inclusions of different sizes. FIG. 2a shows the results for scattering inclusions with $\mu_s'$=1.76 mm$^{-1}$. FIG. 2b shows the results for absorbing inclusions with $\mu_a$=0.029 mm$^{-1}$. In FIG. 2a, line L1 is the diffusion curve measured when no inclusion is present while lines L2, L3 and L4 are the diffusion curves measured when cylindrical scattering inclusions having diameters and thickness of 3.6, 5 and 7 mm respectively are placed in the center of the solution. In FIG. 2b, line L1 is the diffusion curve measured when no inclusion is present while lines L2, L3 and L4 are the diffusion curves measured when cylindrical absorbing inclusions having diameters and thickness of 3.6, 5 and 7 mm respectively are placed in the center of the solution.

Figure 3A:
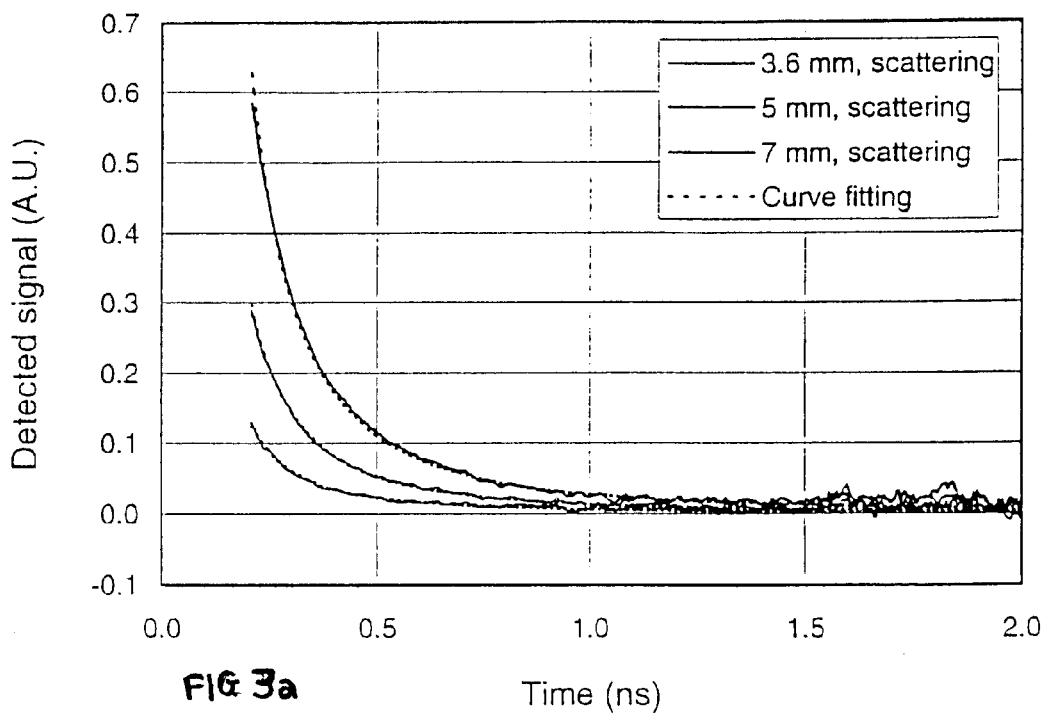
FIGS. 3a and 3b are graphs showing the relative transmissions calculated from the measurements represented in FIGS. 2a and 2b.
Figure 3B:
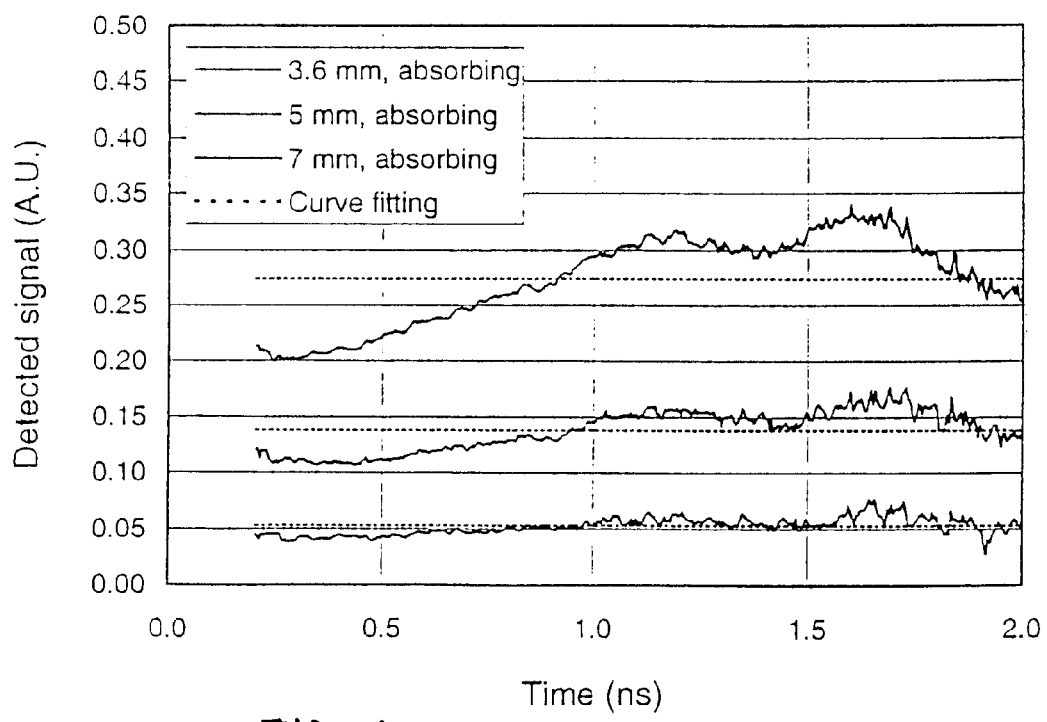

In order to highlight the effect of inclusions on the diffusion curve, the relative transmission can be defined as follows:

$$\eta(t)=-\ln(T_{incl}/T_{ref}), \quad (1)$$

where $T_{incl}$ is the diffusion curve when the inclusion is present, and $T_{ref}$ is the diffusion curve without inclusion. The relative transmissions $\eta(t)$, calculated from the measurement presented in FIGS. 2a and 2b, are shown in FIG. 3. From FIG. 3, it is clear that a temporal signature exists and facilitates the differentiation between the two types of inclusion. FIGS. 3a and 3b illustrate relative transmissions obtained through a 20 mm thick scattering solution ($\mu_s'$=0.97 mm$^{-1}$, $\mu_a$=0.002 mm$^{-1}$) containing inclusions of different sizes. FIG. 3a shows the results for scattering inclusions with $\mu_s'$=1.76 mm$^{-1}$. FIG. 3b shows the results for absorbing inclusions with $\mu_a$=0.029 mm$^{-1}$.

It is convenient to model the relative transmission $\eta(t)$ by an analytical expression. Curve fitting will then be possible on experimental measurements and few numerical values will characterize the change in the diffusion curve. The model must separate the scattering and absorption components and ideally, only one parameter should describe each effect. Such an ideal situation is possible.

According to the present invention, when the inclusion differs from the solution only by its scattering coefficient, the function $\eta(t)$ can be modeled as follows:

$$\eta(t)=A_d(t_o/t)^2 \quad (2)$$

where $A_d$ is a constant representing the amplitude of effect of the inclusion, and $t_o$ is an arbitrary constant that makes $A_d$ dimensionless. It is convenient to choose to to be approximately equal to the time at which the maximum of the diffusion curve occurs. The dotted lines on FIG. 3a represents the curve fitting of the equation (2) on the experimental data.

On the other hand, when the inclusion differs from the solution only by its absorption coefficient, the function $\eta(t)$ is almost time-independent and equal to $A_d$, a constant describing the amplitude of the inclusion effect:

$$\eta(t)=A_a \quad (3)$$

Once again the dotted lines on the FIG. 3b represents the curve fitting of equation (3) on the experimental data.

For an arbitrary inclusion, it has been assumed that the function $\eta(t)$ can be properly modeled as follows:

$$\eta(t)=A_d(t_o/t)^2+A_a \quad (4)$$

where $A_d$ and $A_a$ are associated to the diffusion and absorption phenomenon respectively. Performing a curve fitting of this analytical function on experimental data provides $A_d$ and $A_a$ which are proportional to the scattering and absorption properties respectively.

Figure 4A:
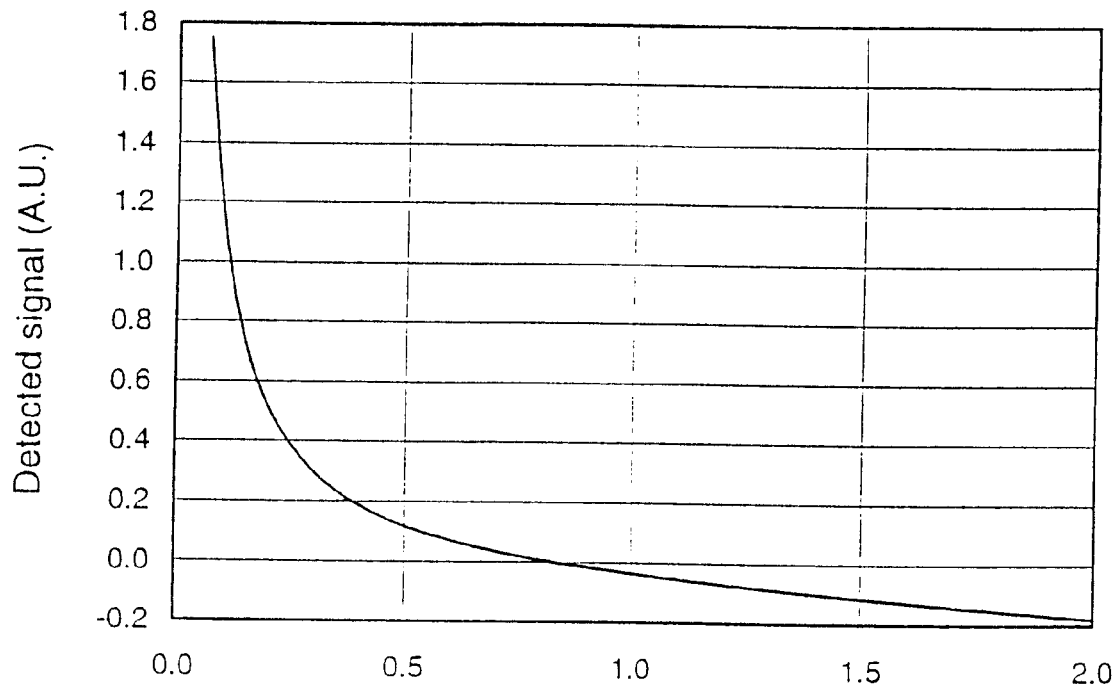
FIGS. 4a and 4b are the theoretical transmissions corresponding to homogeneous cases resulting from a uniform increase of the scattering (a) and absorption (b) coefficients.
Figure 4B:
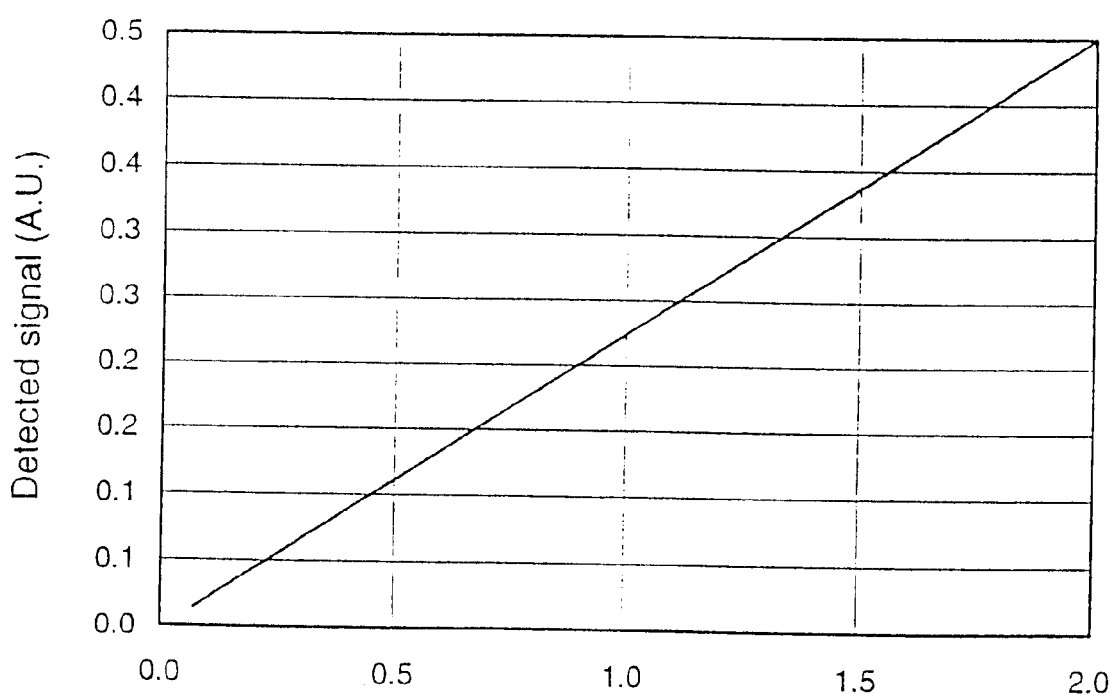

It is important to point out that the method of the present invention permits one to account for the inhomogeneous nature of the geometry. For comparison, FIGS. 4a and 4b show the theoretical relative transmissions $\eta(t)$ corresponding to homogeneous cases, i.e, the $\eta(t)$ resulting from a uniform increase of the scattering and absorption coefficients. The temporal signatures are significantly different from those obtained experimentally for inhomogeneous cases. The theoretical relative transmissions $\eta(t)$ are calculated for a 20 mm thick homogeneous slab ($\mu_s'$=0.97 mm$^{-1}$, $\mu_a$=0.002 mm$^{-1}$). FIG. 4a shows the effect of a homogeneous increase of the scattering coefficient to $\mu_s'$=1.10 mm$^{-1}$. FIG. 4b shows the effect of a homogeneous increase of the absorption coefficient to $\mu_a$=0.003 mm$^{-1}$.

The technique has been successfully tested on data obtained from the scanning of diffusing cells containing small inclusions. FIGS. 5 and 6 show images corresponding to the scanning of a diffusing cell containing a scattering and absorbing inclusion, respectively. For each of the pixels, a pair of values $A_d$ and $A_a$ is obtained from a curve fitting. Thus, for each scan two images are generated: one representing the spatial distribution of $A_d$ values and the other representing the spatial distribution of $A_a$ values. Images generated using the standard curve fitting method, described previously, are also shown for comparison.

Figure 5A:
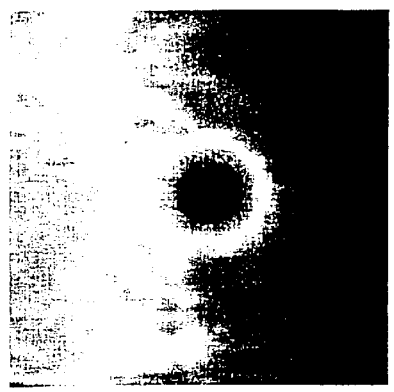
FIG. 5a is an imaging result of a 5 mm scattering inclusion corresponding to the total time-integration of the diffusion curves.
Figure 5B:
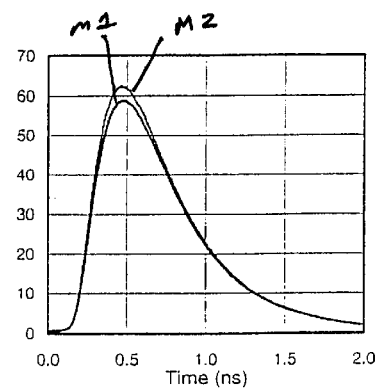
FIG. 5b is a graph depicting diffusion curves corresponding to the image center and a reference background pixel.
Figure 5C:
FIG. 5c is an imaging result of a 5 mm scattering inclusion corresponding to the spatial distributions of the curve fitted absorption coefficient using the homogeneous diffusion model.
Figure 5D:
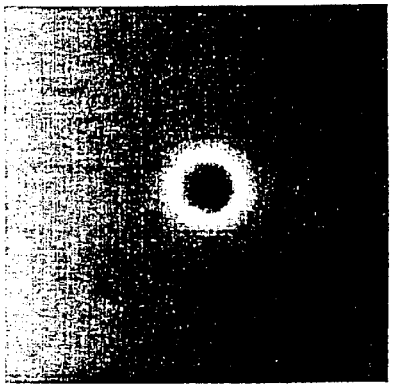
FIG. 5d is an imaging result of a 5 mm scattering inclusion corresponding to the curve fitted scattering coefficient using the homogeneous diffusion model.
Figure 5E:
FIG. 5e is an imaging result of a 5 mm scattering inclusion corresponding to the absorption FIDM parameter.
Figure 5F:
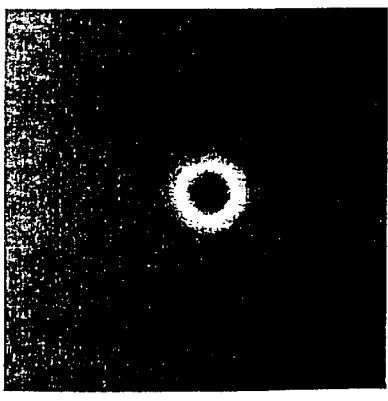
FIG. 5f is an imaging result of a 5 mm scattering inclusion corresponding to the scattering FIDM parameter.

FIGS. 5a–f show imaging results of a 5 mm scattering inclusion ($\mu_s'$=1.76 mm$^{-1}$, $\mu_a$=0.002 mm$^{-1}$) embedded at the center plane of the 20 mm thick scattering cell ($\mu_s'$=1.13 mm$^{-1}$, $\mu_a$=0.002 mm$^{-1}$). FIG. 5a shows an image (40×40 mm) corresponding to the total time-integration of the diffusion curves. FIG. 5b shows the diffusion curves corresponding to the image center (weaker curve M1) and a reference background pixel (stronger curve M2). FIGS. 5c and 5d show the spatial distributions of the curve fitted absorption coefficient, and the curve fitted scattering coefficient, respectively, using the homogeneous diffusion model. FIGS. 5e and 5f show the absorption FIDM parameter $A_a$ and scattering FIDM parameter $A_d$, respectively.

Figure 6A:
FIG. 6a is an imaging result of a 5 mm absorbing inclusion corresponding to the total time-integration of the diffusion curves.
Figure 6B:
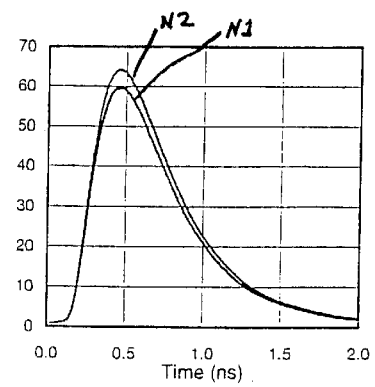
FIG. 6b is a graph depicting diffusion curves corresponding to the image center and a reference background pixel.
Figure 6C:
FIG. 6c is an imaging result of a 5 mm absorbing inclusion corresponding to the spatial distributions of the curve fitted absorption coefficient using the homogeneous diffusion model.
Figure 6D:
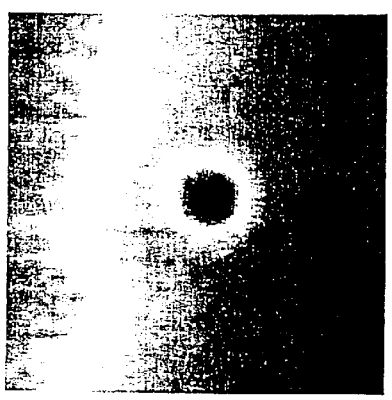
FIG. 6d is an imaging result of a 5 mm absorbing inclusion corresponding to the curve fitted scattering coefficient using the homogeneous diffusion model.
Figure 6E:
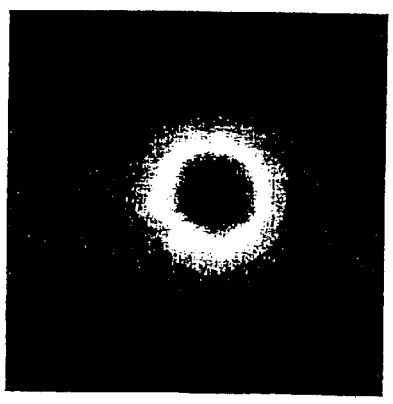
FIG. 6e is an imaging result of a 5 mm absorbing inclusion corresponding to the absorption FIDM parameter.
Figure 6F:
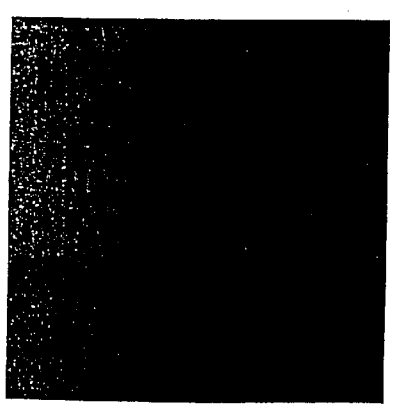
FIG. 6f is an imaging result of a 5 mm absorbing inclusion corresponding to the scattering FIDM parameter.

FIGS. 6a–f show imaging results of a 5 mm absorbing inclusion ($\mu_s'$=1.13 mm$^{-1}$, $\mu_a$=0.015 mm$^{-1}$) embedded at the center plane of the 20 mm thick scattering cell ($\mu_s'$=1.13 mm$^{-1}$, $\mu_a$=0.002 mm$^{-1}$). FIG. 6a shows an image (40×40 mm) corresponding to the total time-integration of the diffusion curves. FIG. 6b shows the diffusion curves corresponding to the image center (weaker curve N1) and a reference background pixel (stronger curve N2). FIGS. 6c and 6d show the spatial distributions of the curve fitted absorption coefficient, and the curve fitted scattering coefficient, respectively, using the homogeneous diffusion model. FIGS. 6e and 6f show the absorption FIDM parameter and scattering FIDM parameter, respectively.

From these FIGS. 5 and 6 it can be seen that the FIDM method provides excellent inclusion type recognition, which can not be achieved using previous methods. In the context of imaging through human tissues, the present invention is a significant step toward tissue differentiation since it properly separates the scattering and absorption properties of a local heterogeneity. Furthermore, the spatial resolution is better for scattering inclusions than for absorbing inclusions. More precisely, the size of an object appears smaller when it is a scattering object. This is explained by the temporal shape of $\eta(t)$: for scattering inclusions, the relative transmission $\eta(t)$ is high only for first arrival photons which are thus favored by the curve fitting process over the late arrival photons. For absorbing inclusions, the function $\eta(t)$ is almost time-independent and the curve fitting process does not favor the first arriving photons. Thus the FIDM technique performs an intrinsic time gating in the case of local variations of the scattering coefficient.

The examples shown in FIGS. 5 and 6 illustrate the power of the method of the present invention for inclusion type recognition.

Figure 7A:
FIG. 7a represents an image of an absorbing and a scattering inclusion embedded in a scattering medium, corresponding to the total time-integration.
Figure 7B:
FIG. 7b represents an image of an absorbing and a scattering inclusion embedded in a scattering medium, corresponding to the absorption FIDM parameter.
Figure 7C:
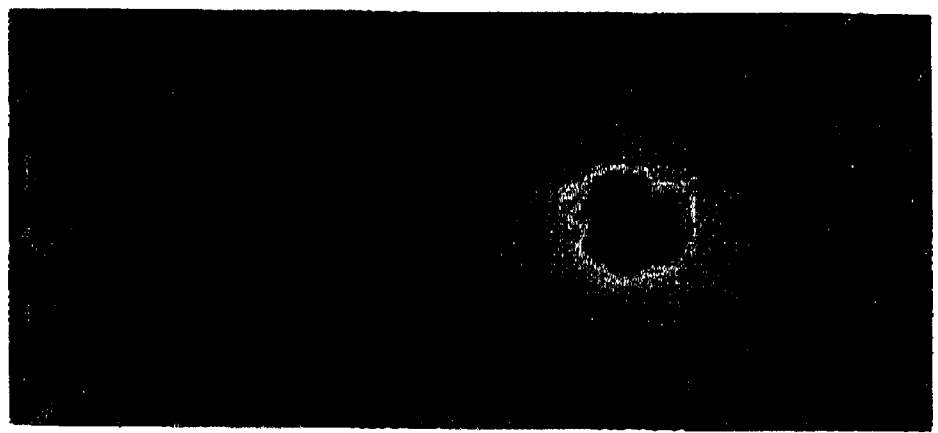
FIG. 7c represents an image of an absorbing and a scattering inclusion embedded in a scattering medium, corresponding to the FIDM scattering parameter.

A further example is shown in FIGS. 7a–c where two inclusions were embedded in a 50 mm-thick homogeneous scattering medium ($\mu_s'$=1.13 mm$^{-1}$ and $\mu_a$=0.002 mm$^{-1}$). The total image is 50 by 25 mm. The inclusion at the left is absorbing having optical coefficients $\mu_s'$=1.13 mm$^{-1}$ and $\mu_a$=0.015 mm$^{-1}$, it has a cylindrical shape with a diameter of 7 mm and a thickness of 7 mm. The inclusion at the right is scattering having optical coefficient $\mu_s$=2.85mm$^{-1}$ and $\mu_a$=0.002 mm$^{-1}$, it has a cylindrical shape with a diameter of 10 mm and a thickness of 7 mm. The top image has been obtained by performing a total time-integration of the measured diffusion curves. The central and bottom images correspond to the spatial distribution of the absorption FIDM parameter $A_a$ and the scattering parameter $A_d$ respectively. The result of FIG. 7 clearly illustrates the power of the present invention for separating the absorption and scattering properties of an inhomogeneous scattering medium.

Other examples are summarized in Table 1, where a diffusion ratio defined as $$R=|A_d|/(|A_d|+|A_a|),$$

has been calculated for on-axis diffusion curve measurements performed on a diffusing cell containing different inclusions. The diffusion ratio R is in the range 0 to 1. An R value close to 1 indicates that the inclusion is diffusing while an R value close to 0 indicates an absorbing inclusion. As can be seen from Table 1, the correlation between the R values and the inclusion type is excellent. For the last three inclusions in Table 1, which are three mixed inclusions of different sizes but with the same optical parameters, approximately the same value has been obtained.

The technique of the present invention also has significant advantages over previous curve fitting techniques in that the mathematical expression is extremely simple. There is a linear dependence of the two parameters $A_d$ and $A_a$ on experimental measurement $\eta$, facilitating a linear curve fitting process which can be calculated significantly faster. For example, the images generated with the standard curve fitting method shown in FIGS. 5 and 6 took 20 minutes to calculate while those obtained with the FIDM technique took approximately 3 seconds.

TABLE I

| Type | $\mu_s'$ (mm$^{-1}$) | $\mu_a$ (mm$^{-1}$) | dimension (mm) | R |
|---|---|---|---|---|
| diffusing | 0.45 | 0.002 | 7 | 0.90 |
| diffusing | 0.45 | 0.002 | 5 | 0.98 |
| diffusing | 0.45 | 0.002 | 3.6 | 0.96 |
| diffusing | 1.36 | 0.002 | 7 | 0.97 |
| diffusing | 1.36 | 0.002 | 5 | 0.79 |
| diffusing | 1.36 | 0.002 | 3.6 | 0.94 |
| diffusing | 1.76 | 0.002 | 7 | 0.96 |
| diffusing | 1.76 | 0.002 | 5 | 0.93 |
| diffusing | 1.76 | 0.002 | 3.6 | 0.89 |
| diffusing | 2.85 | 0.002 | 7 | 0.95 |
| diffusing | 2.85 | 0.002 | 5 | 0.99 |
| diffusing | 2.85 | 0.002 | 3.6 | 1.00 |
| absorbing | 1.13 | 0.022 | 7 | 0.13 |
| absorbing | 1.13 | 0.022 | 5 | 0.11 |
| absorbing | 1.13 | 0.022 | 3.6 | 0.11 |
| absorbing | 1.13 | 0.015 | 7 | 0.07 |
| absorbing | 1.13 | 0.015 | 5 | 0.06 |
| absorbing | 1.13 | 0.015 | 3.6 | 0.02 |
| absorbing | 1.13 | 0.036 | 7 | 0.06 |
| absorbing | 1.13 | 0.036 | 5 | 0.07 |
| absorbing | 1.13 | 0.036 | 3.6 | 0.09 |
| mixed | 1.76 | 0.022 | 7 | 0.21 |
| mixed | 1.76 | 0.022 | 5 | 0.24 |
| mixed | 1.76 | 0.022 | 3.6 | 0.23 |

Having described several embodiments of the method of optical imaging through scattering media in accordance with the present invention, it is believed that other modifications, variations and changes will be suggested to those skilled in the art in view of the description set forth above. It is therefore to be understood that all such variations, modifications and changes are believed to fall within the scope of the invention as defined in the appended claims.

What is claimed is:

1. A method of differentiation between scattering and absorption in a scattering medium having a scattering property and an absorption property, comprising the steps of:

measuring time-dependent diffusion curves through a thick scattering medium for a set of sample positions with respect to a laser beam and point detection;

calculating time-dependent quantities, based on said diffusion curves, representing variations of said diffusion curves from sample positions, from one sample position to a next sample position;

providing an empirical model describing said quantities;

performing a curve fitting process to obtain a first parameter relating to a variation of said scattering property of a local heterogeneity and a second parameter relating to a variation of said absorption property of said local heterogeneity; said first and second parameters being defined by said empirical model; and plotting spatial distribution of said first and second parameters resulting from said curve fitting process.

2. A method of differentiation as recited in claim 1, wherein said scattering medium is a biological tissue.

3. A method of differentiation as recited in claim 2, wherein said differentiation between scattering and absorption properties is used as a method for tissue differentiation.

4. A method of differentiation as recited in claim 1, wherein said time-dependent quantities representing diffusion curve variations are the relative transmissions $\eta(t)$ defined as:

$$\eta(t) = -\ln(T/T_{ref})$$

where T are diffusion curves associated with different sample positions and $T_{ref}$ is a reference diffusion curve.

5. A method of differentiation as recited in claim 4, wherein said reference diffusion curve $T_{ref}$ is a diffusion curve associated with a specific sample position.

6. A method of differentiation as recited in claim 4, wherein when said reference diffusion curve $T_{ref}$ is a mean diffusion curve over a certain range of sample positions.

7. A method of differentiation as recited in claim 4, wherein when said local heterogeneity differs from surrounding medium only in said scattering property, said step of providing said empirical model is provided by modeling said relative transmission $\eta(t)$ as:

$$\eta(t) = A_d(t_o/t)^2,$$

where $A_d$ is a dimensionless parameter associated with variations of said scattering property and $t_o$ is a constant having units of time.

8. A method of differentiation as recited in claim 7, wherein $t_o$ is selected to be approximately equal to a time at which a maximum of said diffusion curves occur.

9. A method of differentiation as recited in claim 4, wherein when said local heterogeneity differs from surrounding medium only in said absorption property, said step of providing said empirical model is provided by modeling said relative transmission $\eta(t)$ as:

$$\eta(t) = A_a,$$

where $A_a$ is a dimensionless parameter associated with variations of said absorption property.

10. A method of differentiation as recited in claim 4, wherein when said local heterogeneity differs from surrounding medium in both said scattering property and said absorption property, said step of providing said empirical model is provided by modeling said relative transmission $\eta(t)$ as:

$$\eta(t) = A_d(t_o/t)^2 + A_a,$$

where $A_d$ is a dimensionless parameter associated with variations of said scattering property, $t_o$ is a constant having units of time, and $A_a$ is a dimensionless parameter associated with variations of said absorption property.

11. A method of differentiation as recited in claim 10, wherein $t_o$ is selected to be approximately equal to a time at which a maximum of said diffusion curves occur.

12. A method of differentiation as recited in claim 10, comprising the further step of calculating a ratio based on said parameters $A_d$ and $A_a$ resulting from said curve fitting, said ratio allowing for quantitative comparisons between scattering and absorption variations.

13. A method of differentiation as recited in claim 12, wherein said ratio is defined as:

$$R = |A_d|/(|A_d| + |A_a|).$$

14. A method of differentiation as recited in claim 1, comprising the further step of calculating a ratio based on said parameters resulting from said curve fitting, said ratio allowing for quantitative comparisons between scattering and absorption variations.

* * * * *